United States Patent
Frankenberger et al.

(10) Patent No.: US 8,749,768 B2
(45) Date of Patent: Jun. 10, 2014

(54) SENSOR FOR CHECKING VALUE DOCUMENTS

(75) Inventors: Jorg Frankenberger, Markt Schwaben (DE); Wolfgang Deckenbach, Schechen (DE); Urs Hennerkes, Furstenfeldbruck (DE); Wolfgang Rauscher, Parkstetten (DE)

(73) Assignee: Giesecke & Devrient GmbH, Munich (DE)

( * ) Notice: Subject to any disclaimer, the term of this patent is extended or adjusted under 35 U.S.C. 154(b) by 0 days.

(21) Appl. No.: 13/515,720

(22) PCT Filed: Dec. 16, 2010

(86) PCT No.: PCT/EP2010/007703
§ 371 (c)(1),
(2), (4) Date: Jun. 13, 2012

(87) PCT Pub. No.: WO2011/072862
PCT Pub. Date: Jun. 23, 2011

(65) Prior Publication Data
US 2012/0257191 A1   Oct. 11, 2012

(30) Foreign Application Priority Data
Dec. 18, 2009 (DE) .......................... 10 2009 058 804

(51) Int. Cl.
*G06K 9/74* (2006.01)
*G06K 9/00* (2006.01)
*A61B 5/117* (2006.01)

(52) U.S. Cl.
CPC .......... *G06K 9/00046* (2013.01); *A61B 5/1172* (2013.01)
USPC .......................................................... 356/71

(58) Field of Classification Search
CPC ...... G06K 9/74; G06K 9/00046; A61B 5/1172
USPC .......................................................... 356/71
See application file for complete search history.

(56) References Cited

U.S. PATENT DOCUMENTS 3,743,422 A * 7/1973 Wood .............................. 356/71
3,765,749 A * 10/1973 LaMacchia ................... 359/291

(Continued)

FOREIGN PATENT DOCUMENTS

DE   10 2005 029 119 A1   12/2006
DE   20 2007 013 090 U1   1/2008

(Continued)

OTHER PUBLICATIONS

International Search Report for PCT/EP2010/007703, Apr. 4, 2011 (3 pages).
German Search Report for German Patent application 10 2009 058 804.3, Oct. 27, 2010 (4 pages).
IPRP and Written Opinion for PCT/EP2010/007703, Jun. 26, 2012 (11 pages).

(Continued)

*Primary Examiner* — Michael P Stafira
(74) *Attorney, Agent, or Firm* — Workman Nydegger (57) ABSTRACT

A sensor for checking value documents has an illumination device for illuminating a value document, an imaging optic and a detection device. A light source receiver has at least two light sources which have mutually different emission spectra. The illumination device contains a microlens array which contains a multiplicity of microlenses, which with the light source receiver are arranged such that each of the light sources arranged on the light source receiver has exactly one of the microlenses associated therewith.

19 Claims, 4 Drawing Sheets

(56) References Cited

U.S. PATENT DOCUMENTS

| | | | |
|---|---|---|---|
| 6,101,266 A | 8/2000 | Laskowski et al. | |
| 6,381,354 B1* | 4/2002 | Mennie et al. | 382/135 |
| 7,170,074 B2* | 1/2007 | Baudat | 250/556 |
| 8,482,816 B2* | 7/2013 | Dressel | 358/475 |
| 2002/0003619 A1* | 1/2002 | Ahlers et al. | 356/71 |
| 2003/0179364 A1* | 9/2003 | Steenblik et al. | 356/71 |
| 2008/0165346 A1* | 7/2008 | Lundquist et al. | 356/73 |
| 2008/0273255 A1* | 11/2008 | Yang et al. | 359/819 |
| 2009/0224694 A1 | 9/2009 | Horing et al. | |
| 2010/0103483 A1 | 4/2010 | Dressel | |
| 2010/0259749 A1* | 10/2010 | Zoladz et al. | 356/71 |

FOREIGN PATENT DOCUMENTS

| | | |
|---|---|---|
| DE | 10 2007 031 230 B3 | 10/2008 |
| JP | 2005-276849 A | 10/2005 |
| JP | 2006-58488 A | 3/2006 |
| WO | 85/02928 A1 | 7/1985 |
| WO | 97/31340 A1 | 8/1997 |
| WO | 2005/109352 A1 | 11/2005 |

* cited by examiner

SENSOR FOR CHECKING VALUE DOCUMENTS

BACKGROUND OF THE INVENTION

A. Field of the Invention

This invention relates to a sensor for checking value documents and to a method for manufacturing the sensor from a sensor platform, as well as to a sensor family having at least two sensors manufactured from the same sensor platform.

B. Related Art

For checking value documents there are usually employed sensors with which the type of the value documents is determined and/or with which the value documents are checked for authenticity and/or for their state. Such sensors are employed for checking value documents such as e.g. bank notes, checks, identity cards, credit cards, check cards, tickets, vouchers and the like. The check of the value documents is effected in an apparatus for value-document processing, in which one or several different sensors are contained, depending on the value-document properties to be checked. Upon checking, the value documents are usually scanned in one or several tracks, whereby the sensor and the value document are moved relative to each other.

The value documents are frequently checked using optical sensors that capture the light reflected by the value documents. Previous optical sensors have been restricted to the spectral properties of the sensor that are defined upon the development of the sensor, such as e.g. the spectral resolution and the position and width of the spectral region capturable by the sensor. To adapt such an optical sensor to different requirements, e.g. a different spectral region or a different spectral resolution, basic changes of the optical components of the sensor are required. With optical sensors whose spectral selection is effected through different color filters which are respectively arranged in front of a detector, it would e.g. be necessary to replace the color filters to change the capturable spectral region. To increase the spectral resolution in such a sensor, additional detectors with different color filters would have to be installed in the sensor. This is usually hardly possible, however, on account of the limited space within the sensor housing.

It is also known to illuminate a value document by employing several different-colored light sources whose light is directed onto the value document via a common light guide. On account of the relative motion between the sensor and the value document transported past it, however, a minimum distance is required between the light guide and the sensor. Because the light diverges after exiting from the light guide, this minimum distance results in the illuminated region on the value document being relatively large and the illumination intensity accordingly low. Hence, such an illumination is unfavorable when the optical properties of a value document are to be captured in a spatially limited region.

SUMMARY OF THE DISCLOSURE

An object of the present invention is hence to provide a sensor platform for a sensor for checking value documents, from which platform there can be manufactured in a simple manner, for different spectral requirements, different sensors for capturing the optical properties of a value document in a spatially limited region.

The sensor is constructed for checking value documents and contains an illumination device for illuminating a value document to be checked by the sensor, an imaging optic and a detection device. Through the imaging optic the light emitted by the illumination device can be imaged onto the value document to be checked by the sensor. The detection device is constructed for detecting detection light which, upon operating of the sensor, emanates from the value document to be checked when the value document is illuminated by the illumination device.

The illumination device has a light source receiving means on which a multiplicity of light source positions are provided, each of which is constructed for receiving a light source, in particular for receiving a chip-shaped light source. At several of the light source positions of the light source receiving means there is respectively arranged exactly one light source. The light source positions are arranged side by side on the light source receiving means and are defined e.g. by a multiplicity of individual depressions by which exactly one light source can respectively be received. Preferably, the light sources are of chip-shaped construction and the depressions so constructed that one chip-shaped light source is respectively insertable therein. However, the light source positions can also be defined by elevations and/or by electrical contact areas, which the light source receiving means can have, and which are constructed for receiving a chip-shaped light source. To obtain a one-to-one association between the microlenses and the light sources to be arranged at the light source positions, the arrangement of the microlenses in the microlens array and the arrangement of the light source positions on the light source receiving means are identical.

At least two of the light sources arranged on the light source receiving means have mutually different emission spectra. This means that at least one of the light sources has an emission spectrum whose maximum lies at a different wavelength compared to the maxima of the emission spectra of the other light sources which are arranged on the light source receiving means. For example, each light source is constructed for emitting an emission line at a certain wavelength. Preferably, the illumination device has a multiplicity of different light sources, i.e. a multiplicity of light sources with mutually different emission spectra whose intensity maxima lie at different wavelengths. In particular, there are arranged on the light source receiving means a multiplicity of light sources whose emission spectra lie in the visible spectral region, and/or a multiplicity of light sources whose emission spectra lie in the infrared spectral region and/or whose emission spectra lie in the ultraviolet spectral region. As light sources there are preferably used light-eradiating diodes, for example light-emitting diodes (LED), in particular semiconductor light-emitting diodes or organic light-emitting diodes (OLED), and/or laser diodes, in particular vertical-cavity surface-emitting lasers (VCSEL).

Moreover, the illumination device of the sensor has a microlens array which contains a multiplicity of microlenses. The microlens array and the light source receiving means are arranged relative to each other such that each of the light sources arranged on the light source receiving means has exactly one of the microlenses associated therewith. Upon operating of the sensor the emission light of each of the light sources is thus collected by exactly one microlens of the microlens array. Each of these microlenses, in so doing, collects only the emission light of exactly one of the light sources. By the microlens associated with the respective light source the emission light of each of the light sources is collected with high efficiency.

Preferably, the microlenses are arranged in the microlens array in the same one- or two-dimensional grid as the light source positions are arranged on the light source receiving means. In particular, the microlens array is constructed as a one-pieced body which preferably has fastening means which are an integral part of the microlens array, in particular of the one-pieced body. The light source receiving means has a counter-piece matching the fastening means of the microlens array. The fastening means of the microlens array are constructed e.g. as fastening pins or as holes for receiving fastening pins which are provided on the light source receiving means. In particular, all microlenses of the microlens array are arranged coplanarly with each other. Preferably, all microlenses of the microlens array are identically constructed to guarantee a greatest possible variability in the arrangement of the light sources on the light source receiving means. In particular, all microlenses have for this purpose the same form and/or the same focal length. Alternatively, some microlenses of the microlens array can also have a form and/or focal length deviating from the remaining microlenses. There could thus be obtained e.g. an individual adaptation of the microlenses to the optical properties of the light sources with which they are associated and for whose light collection they are provided.

Employment of the microlens array results in great advantages in comparison to an illumination device wherein a single lens is employed for each light source. For in this case an individual mount would have to be provided for each of the single lenses, and the exact positioning relative to the respective light source ensured upon the fastening of the single lenses. In so doing, it may be necessary that the exact position and/or orientation of the single lenses must be subsequently adjusted. In contrast, upon employment of a microlens array having exactly one microlens for each light source, a single exact positioning is sufficient. This positioning can be effected through the fastening means of the microlens array which are connected to the corresponding counter-pieces of the light source receiving means. The manufacture of the sensor can hence be effected much more simply and without adjustment. In contrast to the realization of a corresponding illumination device with single lenses which must be individually mounted and whose arrangement always leaves interstices, the microlens array moreover involves no or only a minimal interstice between the individual microlenses. Because the microlens array is constructed as a one-pieced body, the microlenses can pass directly into each other. There can hence be obtained by the microlens array quasi an area-covering light collection. There can hence be formed by the microlens array an illumination device that has a high light collection efficiency and is very compact.

The sensor moreover has an imaging optic which is constructed for imaging the emission light of each of the light sources, after it passes through the respective microlens, onto a value document to be checked by the sensor. The microlenses and the imaging optic are arranged relative to each other such that the emission light of each of the light sources can be imaged by the respectively associated microlens and the imaging optic onto a value document that is to be captured by the sensor. The imaging optic preferably has one or several refractive and/or diffractive optical elements which image the illumination light onto the value document. Preferably, the imaging optic is constructed as an imaging lens. To image the light emitted by the different light sources of the illumination device onto the same illuminated region of the value document to a great extent, the imaging optic is preferably so arranged that the illuminated region of the value document lies precisely or approximately at the focal point of the imaging optic. It can thereby be achieved that in spite of the illumination of the value document with different light sources, the same region of the value document to be checked can always be illuminated and detected by the detection device.

The imaging optic is arranged on the side of the microlens array facing the value document. The imaging optic is constructed for imaging the emission light of each of the light sources, after it passes through the respective microlens, onto a value document to be checked by the sensor. The light emitted by the illumination device is imaged by the imaging optic via a defined ray path onto the illuminated region of the measuring plane or of the value document. Because an imaging of the illumination light onto the value document is effected, the illuminated region of the value document is clearly defined and spatially limited. This constitutes an advantage compared with a direct illumination of the value document by the light sources (without an optic therebetween) and compared with a simple light guide optic (without an imaging optic), through which the light is not imaged, but rather brought onto the value document by the light guide without a defined ray path.

For the sensor there is provided a control device which is adapted to successively switch the light sources of the illumination device on and off again in order to successively illuminate the value document with different emission spectra. The control device can be constructed as part of the sensor, but it can also be constructed as an external control device, e.g. as part of an apparatus for value-document processing in which the sensor is installed. The control device is adapted to drive the illumination device of the sensor, in particular the light sources, and the detection device of the sensor. Upon operating of the sensor the control device successively switches the light sources on and off again, for example such that exactly one of the light sources is switched on at any time. At one or several of the times, however, several of the light sources can also be switched on simultaneously, e.g. several light sources with the same emission spectrum. The value document is in this way illuminated successively with the different emission spectra of the different light sources. Moreover, the control device causes the detection device to respectively capture, during the switched-on phase of the light sources, one measured value which corresponds to the light intensity emanating from the value document. Because the detection device respectively senses one measured value in synchronism with the illumination by the light sources, the light intensity emanating from the value document is thus detected for those wavelengths that are predetermined by the emission light of the light sources. Preferably, the sensor has a multiplicity of different light sources which, upon operating of the sensor, are successively switched on and off to capture the spectral intensity distribution of the light emanating from the value document.

The detection device preferably has a spectral sensitivity which is so spectrally broad-band that the emission light of each of the light sources of the illumination device is detectable by the detection device. In particular, at least visible light and/or infrared and/or ultraviolet light is detectable by the detection device. The measured values sensed by the detection device are subsequently evaluated by an evaluation device which can be part of the sensor or is also formed by an external evaluation device. Preferably, there is already effected by the sensor, in particular by an internal evaluation device of the sensor, at least a pre-processing of the measured values. The further evaluation can likewise be effected through the internal evaluation device or alternatively through a central evaluation device of the apparatus in which the sensor is installed. For detecting the remission light the sensor can also contain several identical detection devices, e.g. in order to capture the remission light over a greater angular range. The sensor can also have several different detection devices, e.g. in order to extend the spectral region capturable by the sensor. Said different detection devices can be arranged side by side or one behind the other, e.g. in the form of a sandwich structure.

The invention moreover shows a method for manufacturing a sensor for checking value documents by which the sensor to be manufactured can be tailored to different spectral requirements with little effort.

The sensor is manufactured from a sensor platform. The sensor platform comprises at least the above-mentioned light source receiving means with the multiplicity of light source positions, the microlens array with the multiplicity of microlenses, the imaging optic and the detection device. To form the illumination device, the light source receiving means is equipped with light sources, whereby at several of the light source positions there is respectively arranged exactly one light source. At least two of the light sources, preferably a multiplicity of the light sources, have mutually different emission spectra. For forming the illumination device the microlens array and the light source receiving means are subsequently arranged relative to each other such that each of the light sources arranged on the light source receiving means has exactly one of the microlenses associated therewith and such that, upon operating of the sensor, the emission light of each of the light sources is collected by exactly one microlens of the microlens array. Preferably, the microlens array and the light source receiving means are, in so doing, fastened to each other. For manufacturing the sensor, the imaging optic is moreover arranged relative to the illumination device such that the emission light of each of the light sources received at the light source positions, after passing through the respective microlens, can be imaged by the imaging optic onto the value document to be checked. Moreover, for manufacturing the sensor, the illumination device, the imaging optic and the detection device are arranged relative to each other such that the detection device can detect detection light which, upon operating of the sensor, emanates from the value document illuminated by the illumination device.

Upon configuring of the sensor, illumination sequences are defined, it being defined in particular which light sources are switched on and off for illuminating the value document. The control device is, in so doing, so configured that the light sources of the illumination device, upon operating of the sensor, are successively switched on and off, so that the value document can be successively illuminated with different emission spectra. The control device provided for the sensor can be already configured upon the manufacture of the sensor. It can be provided, however, that the configuration of the control device is only carried out after the completion of the sensor. Further, it can be provided that the configuration of the control device is also changeable after the sensor has been put into operation. Such a reconfiguring after putting into operation can be carried out e.g. by the manufacturer of the sensor or by an operator of the apparatus in which the sensor is installed. Upon reconfiguring it may also be necessary to adapt the driving of the detection device to the driving of the illumination, e.g. when the number of the light sources switched on and off for measurement is changed. Upon reconfiguring, the evaluation device employed for evaluating the sensed measured values must also be adapted to the changed configuration of the control device, e.g. when different light sources are employed for measurement.

The sensor is not constructed for a full-area check of the value document, but rather for checking the value document in one or in several tracks on the value document. In the case of checking in several tracks, there are respectively arranged between the tracks value-document regions which are not checked by the sensor. The regions illuminated for checking the value document form tracks which extend parallel to each other and along the transport direction of the value document. The tracks are distributed discretely on the value document. For each of the tracks there are provided at least an illumination device, an imaging optic and a detection device according to the above description. The illumination sequences preferably succeed one another so fast that the value document is checked quasi continuously along each of the tracks.

Optionally, there can be arranged in front of the detection device a detection optic by which the detection light emanating from the value document is collected and directed onto the photosensitive region. The detection optic can be realized e.g. by refractive or diffractive optical elements or by mirrors. Preferably, the sensor moreover has a housing in which there are arranged the illumination device, the imaging optic and the detection device, optionally also the control device and detection optic.

The sensor is manufactured from a sensor platform which is formed by the light source receiving means, the microlens array, the imaging optic and the detection device. Optionally, the sensor platform also includes the control device, which can be arranged within or outside the housing. However, said device is not necessarily a part of the sensor. Optionally, the sensor platform can also include the housing and/or the detection optic. However, the sensor can also be realized without a housing and/or without a detection optic. Different sensors can be manufactured from the sensor platform, depending on the selection of the light sources with which the light source receiving means is equipped. Depending on the spectral requirements to be met by the sensor to be manufactured, there can be manufactured from the same sensor platform a first-type sensor which is constructed for checking value documents by illumination with several first emission spectra, or a second-type sensor which is constructed for checking value documents by illumination with several second emission spectra, at least one of which differs from the first emission spectra.

The invention moreover relates to a sensor family which is formed by several sensors for checking value documents, which are different but manufacturable from the same sensor platform. The sensor family comprises at least one first-type sensor which is constructed for checking value documents by illumination with a multiplicity of first emission spectra, and at least one second-type sensor which is constructed for checking value documents by illumination with a multiplicity of second emission spectra, at least one of which differs from the first emission spectra. The at least one first-type sensor and the at least one second-type sensor have for example the same microlens array and/or the same light source receiving means and/or the same imaging optic and/or the same detection device. Preferably, the at least one first-type sensor and the at least one second-type sensor are manufacturable from the same sensor platform, whereby this sensor platform is formed by the light source receiving means, the microlens array, the imaging optic and the detection device. In this case, the first-type sensors and the second-type sensors have the same light source receiving means on which a multiplicity of light source positions are respectively provided, each of which is constructed for receiving a light source, and/or the same microlens array which respectively has a multiplicity of microlenses, whereby the microlens array and the light source receiving means can be arranged relative to each other such that each of the light source positions is associated with exactly one of the microlenses, and the same imaging optic and the same detection device.

In one embodiment example, the selection of the light sources with which the first-type sensors and the second-type sensors are equipped is also the same. The first-type sensors and the second-type sensors are configured differently, however, so that, upon operating of the second-type sensors, one or several different light sources are switched on and off compared to the operating of the first-type sensors. The second-type sensors are so configured that they employ a different subset of the light sources for checking the value documents compared to the first-type sensors. For example, the second-type sensors check the value documents with light of one or several wavelengths which the first-type sensors do not employ for checking the value documents.

In another embodiment example, the number and selection of the light sources with which the first-type sensors and the second-type sensors are equipped are different. The first-type sensors are e.g. equipped with a first selection of light sources and the second-type sensors with a second selection of light sources which differs from the first selection. In particular, one or several light sources of the second selection respectively have an emission spectrum whose spectral position is different in comparison to the spectral position of all emission spectra of the light sources of the first selection.

Besides the first-type and second-type sensors, the sensor family can also have one or several sensors of one or several further types which are manufactured from the same sensor platform and are likewise constructed for checking value documents. Like the second-type sensors, the sensors of the further types belonging to the sensor family can also either be equipped with the same selection of light sources and be configured differently, or be equipped with a different selection of light sources.

DESCRIPTION OF THE DRAWINGS

Hereinafter, the invention will be explained by way of example with reference to the following figures. There are shown:

FIG. 1a a light source receiving means having a multiplicity of light source positions, and a microlens array associated with the light source receiving means, FIG. 1b the light source receiving means from FIG. 1a having light sources arranged thereon, and the associated microlens array, FIG. 1c a section through an illumination device formed from the light source receiving means, the light sources and the associated microlens array of FIG. 1b, FIG. 2a a sensor manufactured from a sensor platform and employing the illumination device from FIG. 1c for illuminating a value document, FIG. 2b a sensor platform from which different sensors for checking value documents can be manufactured, FIGS. 3a-c a sensor family according to a first embodiment example wherein the first-type sensors and the second-type sensors employ different subsets of the same selection of light sources, FIGS. 4a-b a sensor family according to a second embodiment example wherein the first-type sensors and the second-type sensors are equipped with a different selection of light sources.

DETAILED DESCRIPTION OF PREFERRED EMBODIMENTS

Figures 1A, 1B:
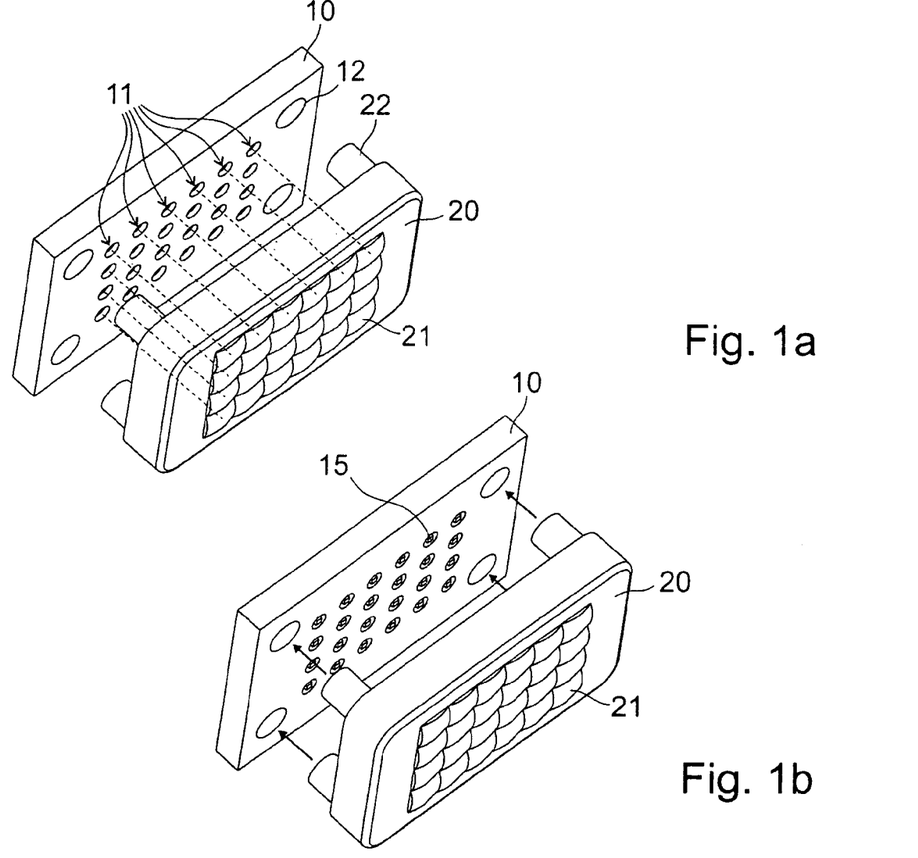

FIG. 1a shows a light source receiving means 10 on which there are provided a multiplicity of light source positions 11, each of which is constructed for receiving a light source 15. The light source receiving means 10 is constructed e.g. as a circuit board and has an electrical wiring structure (not shown) required for operating the light sources 15, which permits a selective driving of each individual light source. The light source positions 11 are formed in this example by depressions in the light source receiving means in which one light source 15 can respectively be fastened. Moreover, FIG. 1a shows a microlens arrays 20 belonging to the light source receiving means 10 and having a multiplicity of microlenses 21. The light source receiving means 10 and the microlens array are mutually coordinated such that each of the light source positions 11 has exactly one of the microlenses 21 associated therewith. For this purpose, the microlenses 21 are arranged within the microlens array in the same two-dimensional grid as the light source positions are arranged on the light source receiving means 10. The microlens array 20 is constructed as a one-pieced body and is formed for example by a glass body or by a transparent plastic body. The diameter of the individual microlenses is e.g. in the μm range or in the mm range.

For forming an illumination device 50, some or all light source positions 11 are respectively provided with one light source 15, cf. FIG. 1b. As light sources 15 there are used e.g. LEDs and/or OLEDs and/or VCSELs. The light sources 15 have a multiplicity of different emission spectra. For example, each of the light sources 15 has a different emission spectrum compared to the remaining light sources 15. Alternatively, however, several identical light sources 15 can also be employed, e.g. to also obtain a sufficient illumination intensity in a spectral region with low-luminosity light sources.

Figure 1C:
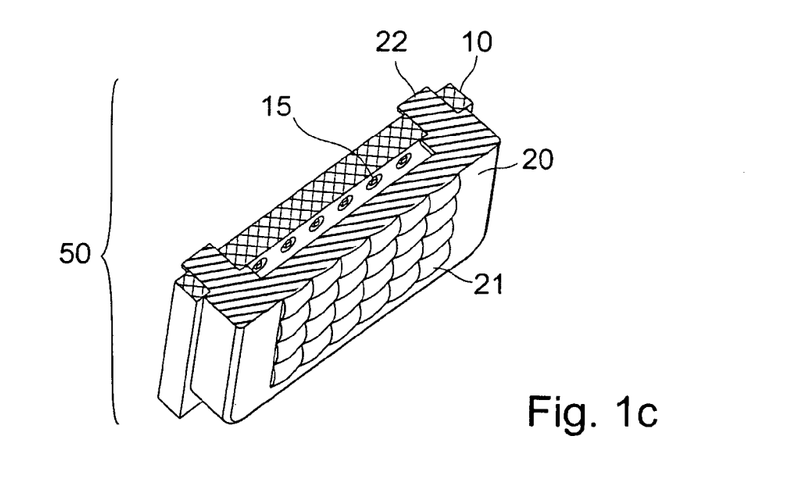

For fastening the microlens array 20, the body of the microlens array 20 is equipped with fastening pins 22 which are inserted into matching holes 12 in the light source receiving means 10. After the insertion of the fastening pins 22, the microlens array 20 and the light source receiving means 10 are fixed to each other, e.g. by a form-fitting connection or by bonding. The light source receiving means 11 with the light sources 15 arranged thereon and the microlens array 20 fastened to the light source receiving means 11 form an illumination device 50, cf. FIG. 1c. The light emitted by the individual light sources 15 is collected by the microlens 21 arranged in front of the respective light source 15. The light source receiving means 10 is so designed that the light source positions 11 are subject to as small tolerances as possible relative to the positions of the holes 12 of the light source receiving means 10. Because the fastening pins 22 are constructed as integral parts of the body of the microlens array 20, their position relative to the microlenses 21 is very precisely defined. In this way, the optimal position of the microlens array 20 relative to the light sources 15 is automatically obtained by the fastening of the microlens array 20 by means of the fastening pins 22. Upon manufacture of the sensor 100, no adjustment of the illumination device 50 is hence required.

The sensor for checking value documents will be explained hereinafter by the example of a remission sensor. The sensor of the invention can also be constructed as a transmission sensor, however. For this purpose, the detection device will be arranged opposite the illumination device, so that the illumination light transmitted through the value document is detected.

Figure 2A:
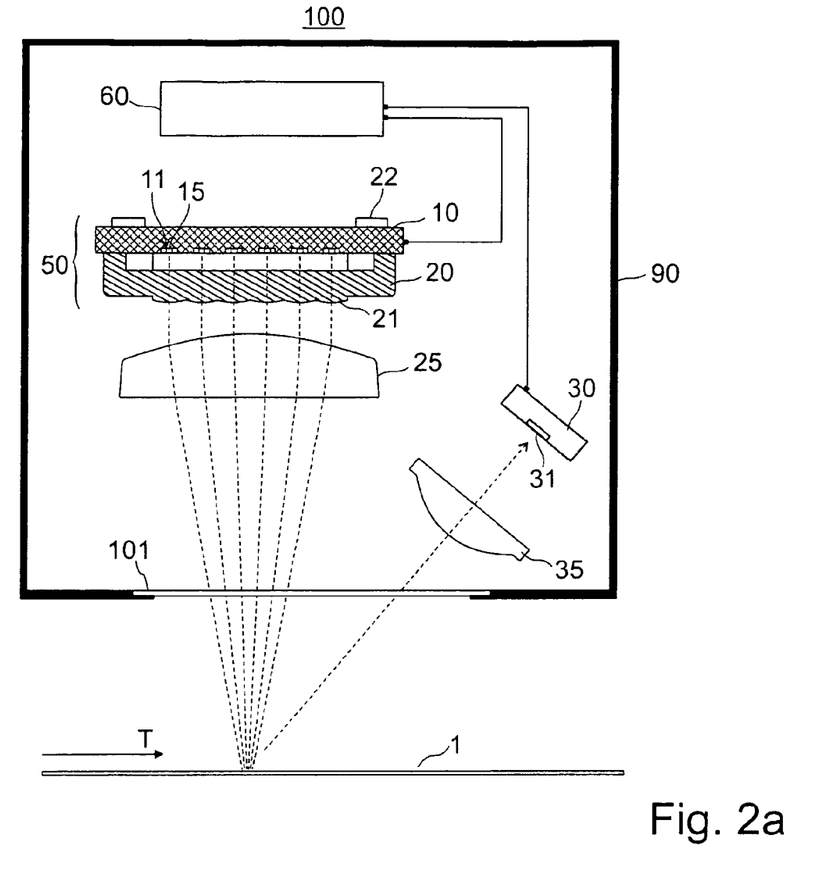

The illumination device 50 is installed in a sensor 100 which is constructed for checking value documents, cf. FIG. 2a. The light emitted by the illumination device 50 is imaged onto the value document 1 by an imaging lens 25. In so doing, the value document 1 is illuminated over a certain region with homogeneous light intensity. To direct the light emitted by the illumination device 50 onto the value document 1, however, there can also be employed as an imaging optic, alternatively to the imaging lens 25, different optical components, e.g. lens systems, diffractive optical components, e.g. a Fresnel lens, or imaging mirrors. Components of the illumination light are remitted by the value document 1, in dependence on the optical properties of the value document 1. The light remitted by the value document 1 is detected using a detection device 30 which has a photosensitive region 31. The detection device 30 can be formed e.g. by a photodiode or a phototransistor. Optionally, there can be arranged in front of the detection device 30 a detection optic 35 by which the light remitted by the value document 1 is collected and directed onto the photosensitive region 31. In the shown example, the illumination light is imaged onto the value document 1 perpendicularly, and the detection device 30 captures the light remitted at an oblique angle. Alternatively, the illumination can also be effected at an oblique angle and the detection device can capture the light remitted in the perpendicular direction or that remitted in the oblique direction.

The sensor 100 has a housing 90 on whose underside there is arranged a transparent window 101. The light emitted by the illumination device 50 is imaged by the window 101 onto a value document 1 to be checked, which is transported past the sensor 100 along a transport direction T. The illumination device 50, in particular the light sources 15, and the detection device 30 are driven by a control device 60, which is arranged within the housing 90 in this example. The control device 60 successively switches the light sources 15 on and off again, for example such that exactly one light source 15 is respectively switched on at any time. During the switched-on phase of the light sources, the detection device 30 respectively captures one measured value which corresponds to the light intensity remitted by the value document 1. The value document 1 is illuminated successively with the different emission spectra of the different light sources 15. Because the detection device 30 respectively senses one measured value in synchronism with the illumination by the light sources 15, the light intensity remitted by the value document 1 is thus measured in each spectral region which the light sources 15 predetermine.

The control device 60 drives the light sources 15 such that the illumination sequence with which the light sources 15 are switched on and off is repeated periodically. For example, the control device 60 can be programmed such that each light source 15 of the illumination device 50 is switched on and off exactly once during each illumination sequence. Alternatively, a light source 15 can also be driven several times per illumination sequence, e.g. in order to compensate the low intensity of a low-intensity light source 15 by multiple measurement. An illumination sequence can include either the driving of all light sources 15 present in the illumination device 50 or only of a subset of the light sources 15 present. After an illumination sequence, i.e. after a measured value has been sensed under illumination with each emission spectrum provided for the measurement, the next illumination sequence starts, in which a measured value is again sensed under illumination with each emission spectrum provided for the measurement, etc. The duration of the illumination sequence is coordinated with the transport speed of the value document 1 such that the different measured values of an illumination sequence stem at least approximately from the same detection region on the value document 1. The path that the value document 1 covers from the beginning to the end of the same illumination sequence is thus much shorter than the length of the detection region. The measured values obtained during an illumination sequence can yield e.g. a spectral dependence of the remission of the respective detection region.

Figure 2B:
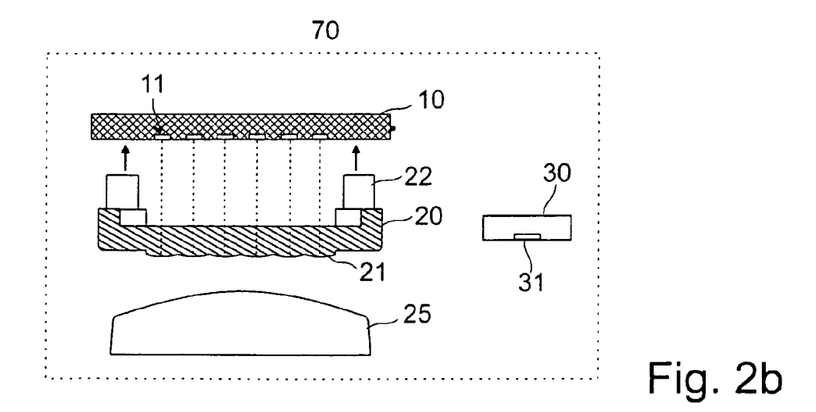

The sensor 100 is manufactured from a sensor platform 70 which consists of the following elements, cf. FIG. 2b: the light source receiving means 10, the microlens array 20, the imaging optic 25 and the detection device 30. Optionally, the sensor platform 70 includes the control device 60 and/or the housing 90 and/or the detection optic 35. The sensor of the invention can also be realized without these elements, however. From the sensor platform 70 different sensors be manufactured, depending on the selection of the light sources 15 with which the light source receiving means 10 is equipped. Depending on the requirements to be met by the sensor to be manufactured, there can be manufactured from the same sensor platform 70 for example either a first-type sensor 100A or a second-type sensor 100B.

Figure 3A:
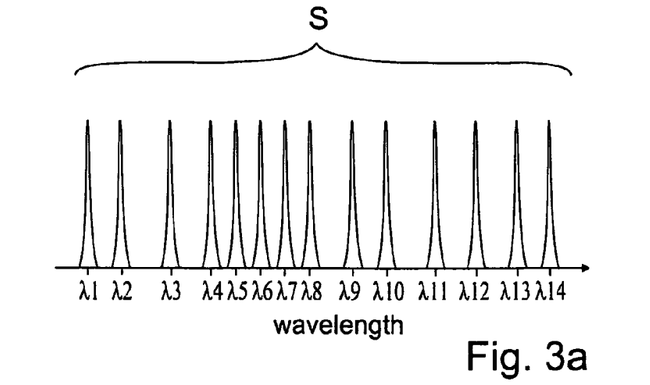
Figure 3B:
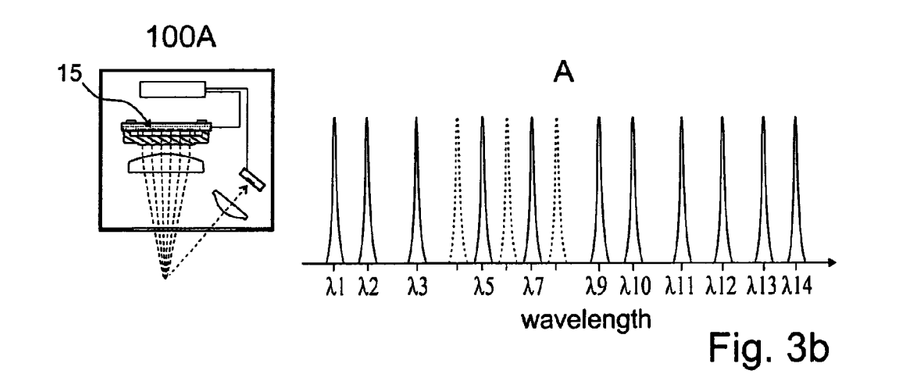
Figure 3C:
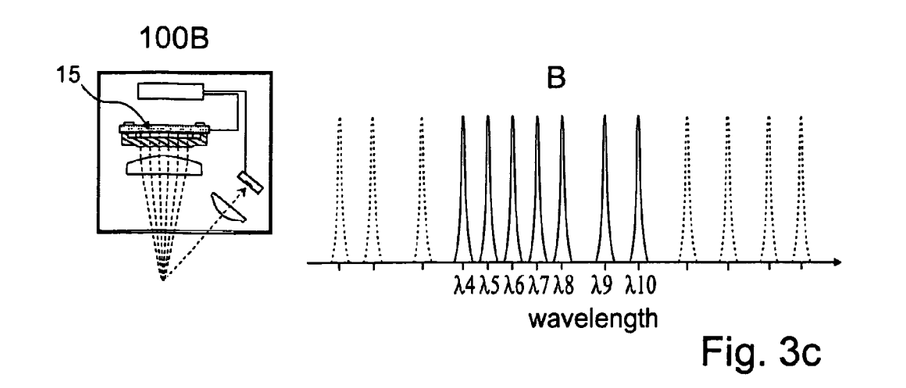

In a first embodiment example, the first-type sensors 100A and the second-type sensors 100B are equipped with the same selection S of light sources 15, cf. FIG. 3a. The selection S of light sources 15 with which the sensor platform 70 is equipped upon manufacture of the sensors 100A and 100B respectively consists of fourteen different light sources 15 in the shown example. The spectral position of the different emission maxima of these light sources 15 is designated as $\lambda 1$ to $\lambda 14$ in FIG. 3a. The emission spectra of the light sources 15 extend e.g. from the ultraviolet through the visible to the near infrared spectral regions. From the selection S, however, the first-type sensors 100A and the second-type sensors 100B employ different subsets of light sources 15. For example, the first-type sensor 100A employs the subset A which consists of the light sources with the wavelengths $\lambda 1$-$\lambda 3$, $\lambda 5$, $\lambda 7$ and $\lambda 9$-$\lambda 14$, cf. FIG. 3b. The second-type sensor 100B employs the subset B which consists of the light sources with the wavelengths $\lambda 4$-$\lambda 10$, cf. FIG. 3c. The control device 60 of the sensor 100A is so configured that the light sources of the wavelengths $\lambda 1$-$\lambda 3$, $\lambda 5$, $\lambda 7$ and $\lambda 9$-$\lambda 14$ are successively switched on and off during an illumination sequence. In contrast, the control device 60 of the second-type sensor 100B is so configured that the light sources of the wavelengths $\lambda 4$-$\lambda 10$ are successively switched on and off during an illumination sequence of the second-type sensor 100B.

Figure 4A:
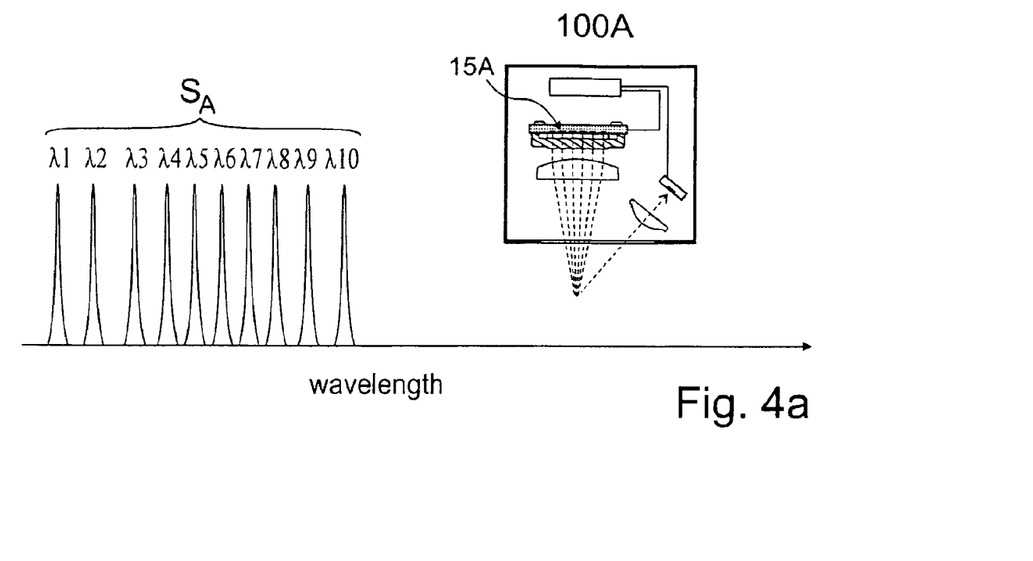
Figure 4B:
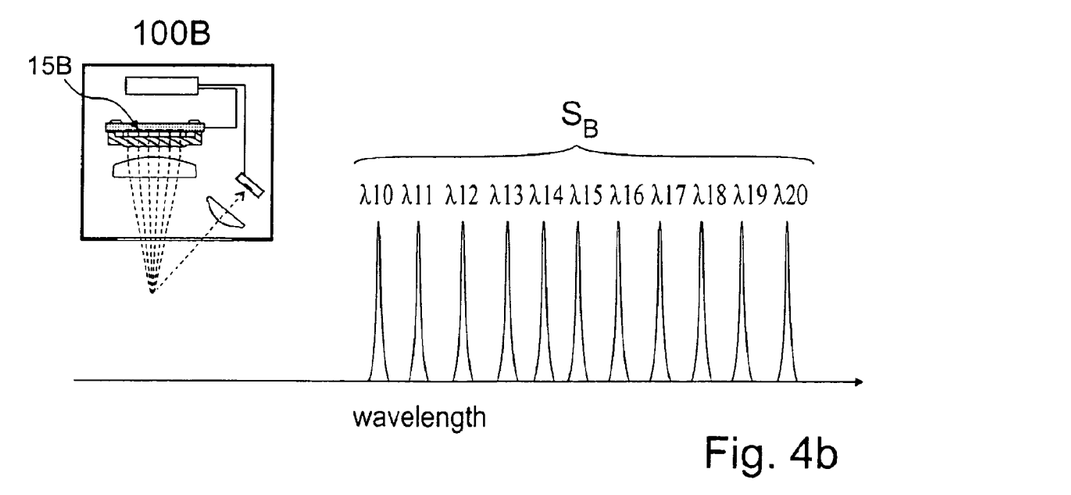

In a second embodiment example, the second-type sensors have a different selection of light sources compared to the first-type sensors 100A. For manufacturing the sensors 100B, the sensor platform 70 is thus equipped with a different selection of light sources 15 compared to the manufacture of the sensors 100A. For example, the first-type sensors 100A are equipped with a first selection $S_A$ of light sources 15A, and the second-type sensors 100B with a second selection $S_B$ of light sources 15B, cf. FIGS. 4a-b. The first selection $S_A$ consists in this example of ten different light sources 15A whose wavelengths are designated as $\lambda 1$-$\lambda 10$. The second selection $S_B$ consists in this example of eleven different light sources 15B whose wavelengths are designated as $\lambda 10$-$\lambda 20$. The light sources 15B here can partly be identical with the light sources 15A.

The invention claimed is:

1. A method for manufacturing a sensor useful for checking value documents, comprising the steps:
   providing a sensor platform, comprising:
   a light source receiver on which there are provided a multiplicity of light source positions, each of the light source positions being configured to receive a light source, and
   a microlens array comprising a multiplicity of microlenses, said microlens array and light source receiver arranged relative to each other such that each of the light source positions is associated with exactly one of the microlenses
   an imaging optic, and
   a detection device, forming an illumination device by:
  providing the light source receiver with light sources, each of the light sources being a light emitting diode, so that at several of the light source positions of the light source receiver there is respectively arranged exactly one light emitting diode, and the emission spectra of at least two of the several light sources being mutually different, and
  arranging the microlens array and the light source receiver provided with the light sources relative to each other such that each of the several light sources has exactly one of the microlenses associated therewith, wherein each of these microlenses collects only emission light of exactly one of the light emitting diodes,
  arranging the illumination device and the imaging optic such that, upon operating of the sensor, a portion of light emitted by each of the several light sources is imaged by the imaging optic onto the same area of a value document to be checked by the sensor, and
  arranging the detection device such that the detection device detects detection light which, upon operating of the sensor, emanates from the value document illuminated by the illumination device, wherein
  each of the light emitting diodes is a chip-shaped light emitting diode, and
  the emission light of each of the chip-shaped light emitting diodes is collected by the microlens associated with the light emitting diode.

2. The method according to claim 1, wherein, upon forming of the illumination device, the light source receiver equipped with the light sources and the microlens array are fastened to each other.

3. The method according to claim 1, wherein there is provided for the sensor a control device which is constructed for driving the light sources, and configuring the control device to successively switch the light sources of the illumination device on and off, so that the value document is illuminated successively with different emission spectra.

4. The method according to claim 1, including manufacturing from the same sensor platform different sensors for checking value documents, and at least one second-type sensor which is configured to check value documents by illumination with several second emission spectra, at least one of which differs from the first emission spectra.

5. A sensor for checking value documents, comprising:
  an illumination device having
  at least two light sources whose emission spectra are mutually different,
  a light source receiver on which there are provided a multiplicity of light source positions, each of the light source positions being constructed for receiving one of the light sources, each of the light sources being a light emitting diode, wherein at several of the light source positions there is respectively arranged exactly one light emitting diode, and
  a microlens array which comprises a multiplicity of microlenses, wherein the microlens array and the light source receiver are arranged relative to each other such that each of the light sources arranged on the light source receiver has exactly one of the microlenses associated therewith, wherein each of these microlenses collects only emission light of exactly one of the light emitting diodes, so that the emission light of each of the light sources is collected by the microlens associated with the light source,
  an imaging optic by which a portion of the light emitted by each of the several light sources is imaged onto the same area of a value document which, upon operating of the sensor, is to be captured by the sensor, and
  a detection device which is configured to detect detection light which, upon operating of the sensor, emanates from the value document illuminated by the illumination device, wherein each of the light emitting diodes is a chip-shaped light emitting diode, and
  the emission light of each of the chip-shaped light emitting diodes is collected by the microlens associated with the light emitting diode.

6. The sensor according to claim 5, wherein there is provided for the sensor a control device which is arranged to successively switch the light sources of the illumination device on and off to thereby successively illuminate the value document with different emission spectra.

7. The sensor according to claim 5, wherein the sensor has a multiplicity of different light sources which, upon operating of the sensor, are successively switched on and off in order to capture a spectral intensity distribution of the light emanating from the value document.

8. The sensor according to claim 5, wherein the microlens array comprises fasteners that fasten the microlens array to the light source receiver.

9. The sensor according to claim 5, wherein the microlens array is constructed as a one-pieced body.

10. The sensor according to claim 5, wherein each of the light source positions is configured to receive a chip-shaped light source.

11. A sensor family comprising at least one first-type sensor as recited in claim 5 and at least one second-type sensor as recited in claim 5, wherein the at least one first-type sensor is arranged to check value documents by illumination with several first emission spectra, and the at least one second-type sensor is arranged to check value documents by illumination with several second emission spectra, at least one of which differs from the first emission spectra.

12. A sensor family according to claim 11, wherein the at least one first-type sensor and the at least one second-type sensor have the same microlens array and/or the same light source receiver and/or the same imaging optic and/or the same detection device.

13. The sensor family according to claim 11, wherein the at least one first-type sensor and the at least one second-type sensor are manufacturable from the same sensor platform, so that the same sensor platform includes at least the same light source receiver, the same microlens array, the same imaging optic and the same detection device.

14. The sensor family according to claim 11, wherein the first-type sensors and the second-type sensors are provided with the same selection of light sources, and the second-type sensors employ a different subset of the light sources for checking the value documents compared to the first-type sensors.

15. The sensor family according to claim 11, wherein the first-type sensors are provided with a first selection of light sources and the second-type sensors are equipped with a second selection of light sources which differs from the first selection.

16. The method according to claim 1, wherein the light emitted by the illumination device is imaged by the imaging optic onto the same illuminated region of a value document to be checked by the sensor.

17. The method according to claim 16, wherein the imaging optic is configured to image the light emitted by the light sources such that the illuminated region lies precisely or approximately at the same focal point of the imaging optic.

18. The sensor according to claim 5, wherein the light emitted by the illumination device is imaged by the imaging optic onto the same illuminated region of a value document to be checked by the sensor.

19. The sensor according to claim 18, wherein the imaging optic is configured to image the light emitted by the light sources such that the illuminated region lies precisely or approximately at the same focal point of the imaging optic.

* * * * *